United States Patent [19]
Fullam

[11] Patent Number: 5,827,483
[45] Date of Patent: Oct. 27, 1998

[54] OIL DIFFUSER WITH DOUBLE BOWL AND FOLDING TRIPOD SUPPORT

[75] Inventor: Philip S. Fullam, Chimayo, N. Mex.

[73] Assignee: New Venture Engineering, Inc., Sante Fe, N. Mex.

[21] Appl. No.: 866,124

[22] Filed: May 30, 1997

[51] Int. Cl.⁶ .................................................. A62B 7/08
[52] U.S. Cl. ..................... 422/122; 248/166; 248/177.1; 248/901; 422/123; 422/125
[58] Field of Search ................................. 422/5, 4, 120, 422/122, 123, 125; 248/163.1, 166, 163.2, 177.1, 901

[56] References Cited

U.S. PATENT DOCUMENTS

| | | |
|---|---|---|
| 2,254,906 | 9/1941 | Petrulis . |
| 3,355,913 | 12/1967 | Frangos . |
| 4,579,717 | 4/1986 | Gyulay ..................................... 422/125 |
| 4,647,428 | 3/1987 | Gyulay ..................................... 422/125 |
| 4,781,895 | 11/1988 | Spector ..................................... 422/125 |
| 4,892,711 | 1/1990 | Tendick, Sr. . |

FOREIGN PATENT DOCUMENTS 2 294 717  7/1976  France .

Primary Examiner—Krisanne Thornton

[57] ABSTRACT

An essential oil diffuser having a compact foldable tripod support is provided to facilitate carrying the diffuser in luggage such as briefcases or handbags. The essential oil diffuser will heat oil to the proper temperature without risk of overheating or burning the oil through combustion. In order to achieve a compact package having a short vertical dimension, the oil bowl must be placed close to the candle flame and so the diffuser includes a double bowl assembly supported by three folding legs. The double bowl assembly has an upper bowl member and a lower plate member separated by a uniform air gap. The lower plate member has a large radial flange extending beyond the perimeter of the upper bowl member, thereby containing spills. The lower flange of the lower plate member also serves as a heat sink, thereby diffusing and dissipating excess heat from the candle by convection and radiation. The upper bowl member is an oil reservoir supported upon the lower plate member by three transversely projecting attachment points and is heated indirectly from the flame through the lower plate member by conduction through the attachment points, by convection and by radiation. The oil diffusing bowl is positioned above a candle supported on a platform attached to the three folding legs of the collapsible tripod. Each folding leg has an upper segment and a lower segment joined by a link bar press-fitted into the lower leg and rotatable on a hinge pin. The upper leg includes a thermal lock expanding in response to heat from the candle. When the leg is above a selected threshold temperature, it is not possible to disjoin the upper leg from the lower leg due to interference from the expanded thermal lock.

20 Claims, 6 Drawing Sheets

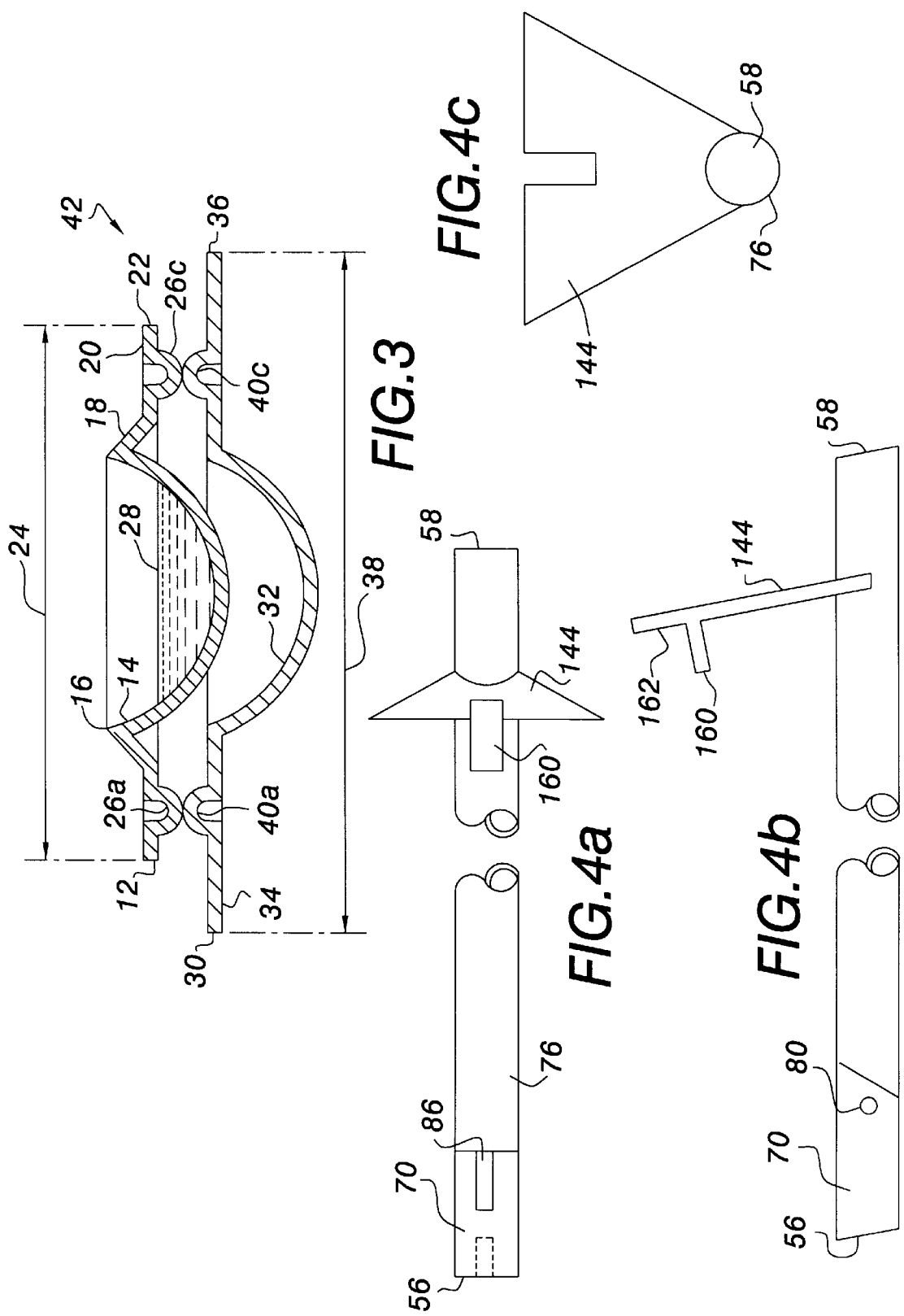

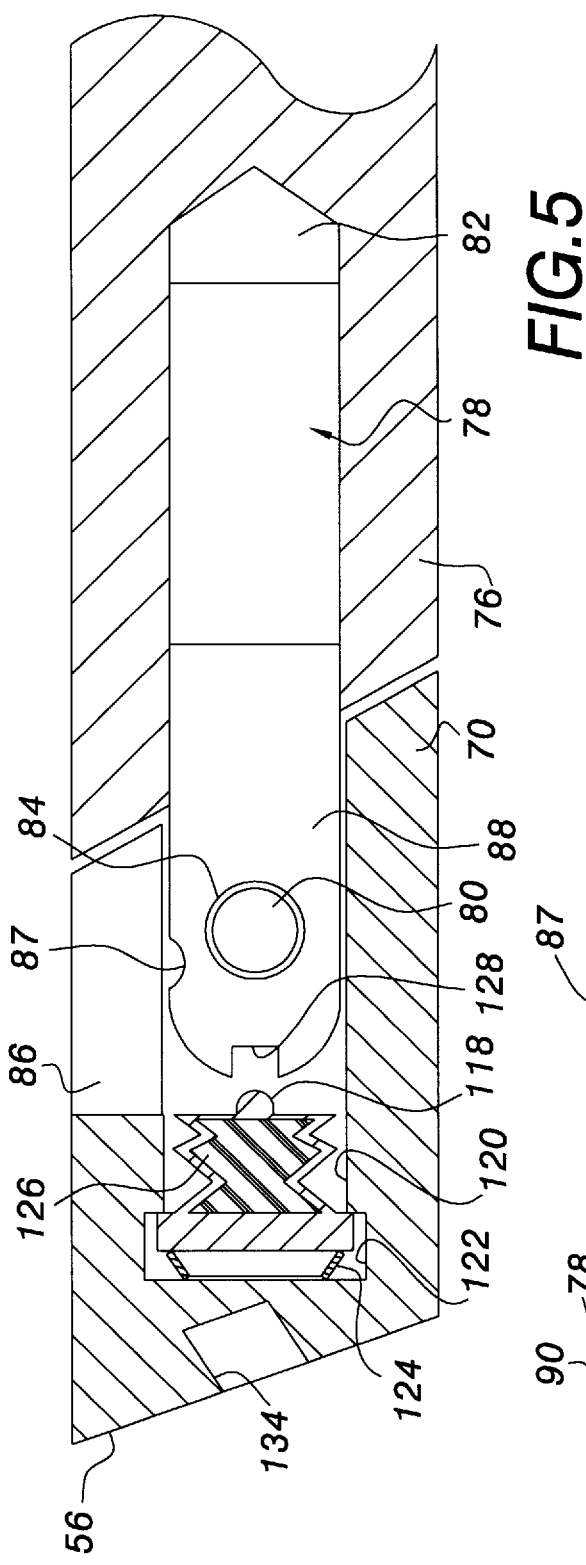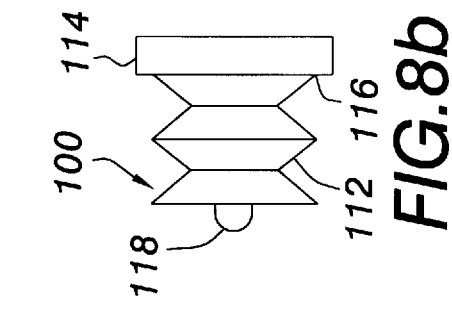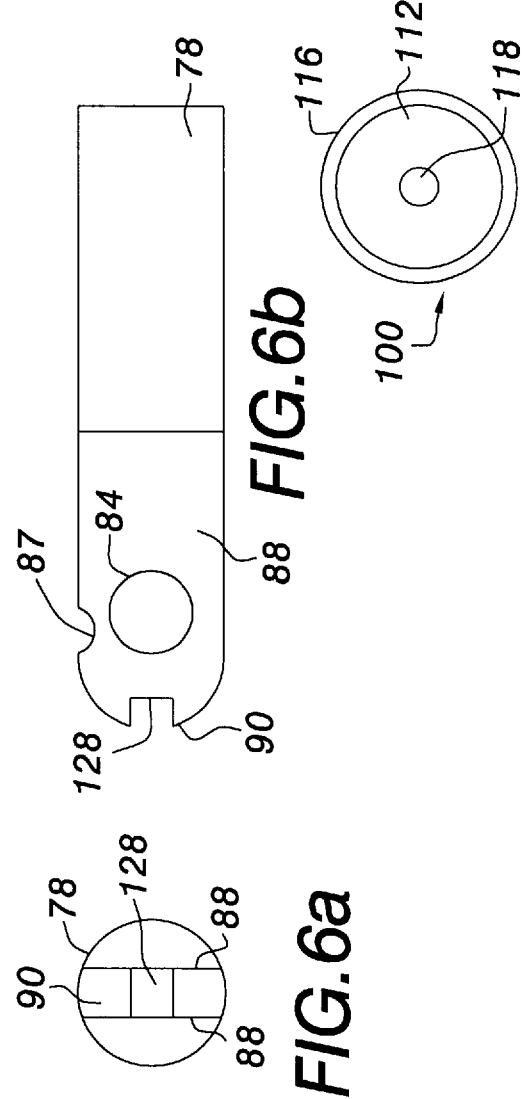

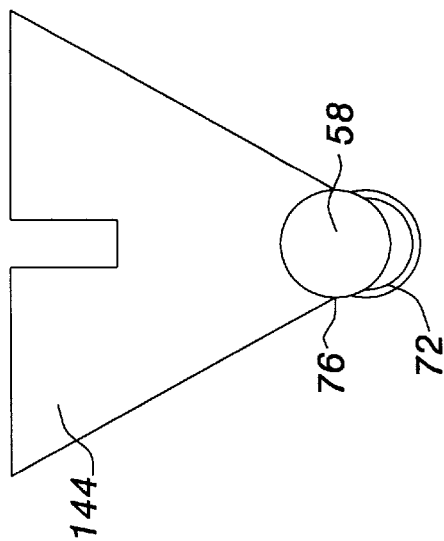
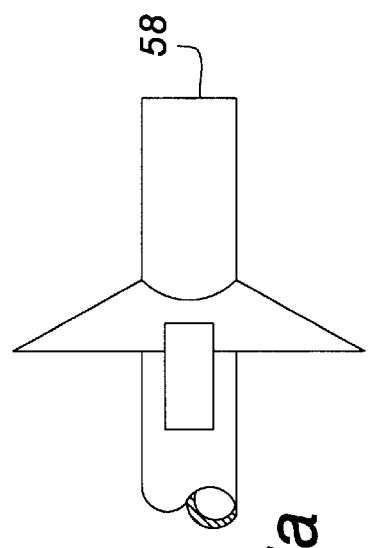
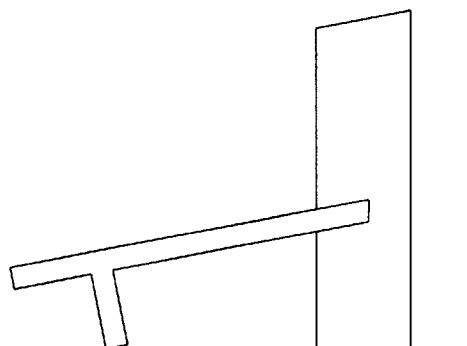
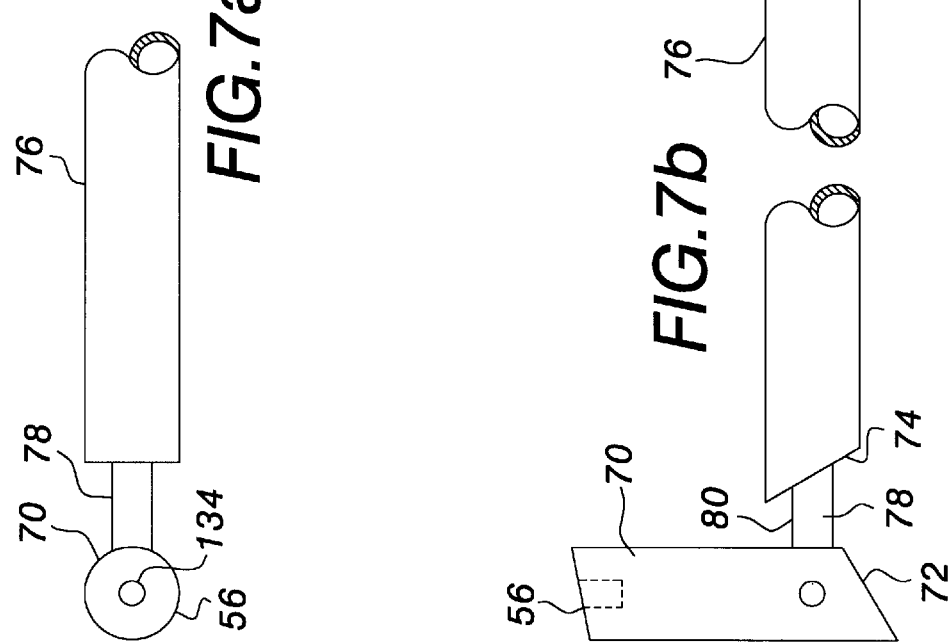

OIL DIFFUSER WITH DOUBLE BOWL AND FOLDING TRIPOD SUPPORT

BACKGROUND OF THE INVENTION

1. Field of the Invention

The present invention relates to fragrance generating devices, and more particularly to a candle heated fragrance generator and a stable, safe, compact, transportable structure for use therewith.

2. Discussion of the Prior Art

A number of devices and methods for generating or dispensing fragrance are known. Devices for imparting a fragrance to an occupied space include aerosol sprays, scented candles, dried flowers in potpourri and scented, diffusible liquids and solids. An especially pleasant way to impart fragrance to a room is through proper heating of essential oils. Chemists have succeeded in analyzing the essential oils from which natural perfumes are made, and in creating thousands of synthetic fragrances, some simulating natural products and others yielding altogether new scents. Heating essential oils is best performed using a bowl or other vessel suspended over a candle by use of a support structure such as a tripod. The prior art tripod structure suspends an oil bowl over a candle flame at a height of four to five inches above the flame. For safety's sake, the tripod should be structurally stable; usually, the overall structure is six to seven inches tall and, at the bottom of the support legs, defines a triangle of perhaps five to six inches on a side, thereby taking up a considerable amount of table top space. By suspending the oil bowl over the candle at a height of between four to five inches, sufficient and proper distance is allowed between the candle flame and the oil bowl bottom, thereby preventing degradation of the oil due to excessive temperature and oil combustion. The problem encountered in using essential oils while away from home is that the pleasant and effective tripod and candle structure of the prior art is bulky, large and not easily transportable. There is a need, therefore, for a safe and transportable apparatus for diffusing fragrances from essential oils, for use when away from home.

In the prior art, portable annular containers have been placed adjacent to light bulbs or the like, whereby heat from the bulb causes a liquid or solid fragrance material to vaporize, thereby providing a fragrance for diffusion into the room. For annular troughs or channels fashioned out of metal and positioned on light bulbs, a disadvantage exists in that an essential oil or other liquid fragrance must be carefully added while the container is adjacent to the light bulb. If the container is filled with the liquid away from the bulb, the container must be carefully transferred to and positioned on the bulb in order to avoid spilling the contents. Once the light bulb is lit, the container heats to a high temperature and, if bumped, can tip and create a messy and hazardous hot oil spill.

In a similar vein, the porous ceramic ring structure of U.S. Pat. No. 4,647,428, to Gyulay, includes a ceramic ring with an annular channel filled with fragrant oil, whereby the ceramic can absorb the oil and reduce the risk of spillage. The Gyulay vaporizer still requires the use of a light bulb, however, and so must be used with an electric lamp in a possibly hazardous manner which the lamp manufacturer could not have foreseen. Use of an electric light also provides none of the aesthetic benefits conferred by the simple and elegant candle flame.

Accordingly, there is a need for a compact, safe and transportable apparatus and method for diffusing essential oils, or the like, and permitting the use of aesthetically pleasing candles as a heat source.

OBJECTS AND SUMMARY OF THE INVENTION

Accordingly, it is a primary object of the present invention to overcome the above-mentioned disadvantages of the prior art by providing a compact, foldable and transportable structure for efficiently and safely heating a fragrance material to a proper temperature for diffusing a fragrance into a room.

A further object of the present invention is to provide a compact essential oil heating structure with a specially adapted oil bowl permitting oil to be heated, but not overheated, when positioned at a short distance above a candle flame.

Another object of the present invention is providing a foldable tripod as a stable and secure platform for heating essential oil while protecting adjacent surfaces from exposure to excess heat from the candle and from inadvertently spilled hot oil.

Yet another object of the present invention is to provide a diffuser having a folding tripod with a temperature responsive mechanical interlock for preventing folding and storage of the tripod while the diffuser is excessively hot.

In accordance with the present invention, a foldable essential oil diffuser having a compact physical size and a small footprint is provided to facilitate carrying the diffuser in luggage such as briefcases or handbags. The compact essential oil diffuser of the present invention will heat the oil to the proper temperature without risk of overheating the oil or burning the oil through combustion. In order to achieve a compact package having a short vertical dimension, the oil bowl must be placed close to the candle flame, potentially resulting in a very high temperature at the bowl to oil interface, leading to degraded oil or combustion of the oil. Overheating the oil ruins it, rendering it useless for generating a fragrance. The compact oil diffuser of the present invention provides a way of controlling the candle heat and the temperature of the oil bowl by dissipating heat from the flame without substantially increasing the overall height of the assembly; the heat is diffused in a double bowl assembly supported by three folding legs. The double bowl assembly includes an upper bowl or plate member and a lower plate member separated by a air gap of uniform spacing. The lower plate member has bowl-shaped indented portion and a large radial flange extending beyond the perimeter of the upper bowl member flange, thereby containing oil spilled from the upper bowl. The lower flange of the lower plate member also serves as a heat sink, thereby diffusing and dissipating excess heat from the candle by convection and radiation. The upper bowl member is an oil reservoir and is supported upon the lower plate member by three transversely projecting attachment points joined by thermally conductive coupling screws, rivets, welds or the like. The upper bowl member is heated indirectly from the flame through the lower plate member by conduction through the attachment points and radiation. The upper bowl member also includes a radially extended flange and a raised reservoir containment wall intermediate the bowl portion and the flange portion to prevent spills from bumps or wicking of oil from the bowl onto the face of the flange. The double bowl assembly is positioned above a candle supported on a plate or platform attached therebelow to the three folding legs of the collapsible tripod. Each folding leg has an upper segment and a lower segment joined by a link bar press-fitted into the lower leg. The link bar rotates on a hinge pin. The upper leg includes a thermal lock expanding in response to heat from the candle and having a locking pin; when the upper leg is above a selected threshold temperature, the thermal lock body to expands and forces the locking pin into a cutout in the link bar, making it impossible to rotate and disjoin the lower leg. Accordingly, the thermal lock prevents a user from inadvertently disassembling and storing the diffuser when the tripod is excessively hot.

In use, the folding essential oil diffuser can be expanded by opening the three folding legs of the tripod structure and positioned on a table top, or the like. The candle is placed on the candle holder plate located in the tripod center, held in place by raised tabs and supported above the surface of the table. Essential oil is poured into the reservoir of the upper bowl and the candle is lit, whereupon flame from the candle heats the lower plate member of the double bowl assembly. The flame's heat is transmitted via radiation, convection and conduction from the lower plate member to the upper bowl and causes the oil in the oil reservoir to vaporize, thus diffusing the fragrant aromas of the essential oil into the air surrounding the diffuser. Heat is also conducted from the lower plate to the upper legs and to the thermal lock body, causing the thermal lock body to expand and forcing a locking pin into a cutout in the link bar situated between the upper leg and the lower leg in each of the three legs of the tripod. When the thermal lock is in the extended position, the link bar cannot rotate about the hinge pin and the legs are locked until such time as the candle flame is extinguished and the lower plate and thermal lock have had sufficient time to cool. The operator may then remove any residual oil from the oil reservoir, whereupon the candle can be removed and the three legs can be folded for storage.

The foregoing and additional objects, features and advantages of the invention will become apparent to those with skill in the art from the following detailed description of a preferred embodiment, taken with the accompanying drawings, wherein like reference numerals in the various drawings identify like components.

BRIEF DESCRIPTION OF THE DRAWINGS

FIG. 3 is a cross-sectional view of the double bowl assembly.

FIG. 4a is an elevation view of the extended leg assembly.

FIG. 4b is a side view of the leg assembly of FIG. 4a rotated 90° about the leg axis.

FIG. 4c is an end view of the leg assembly illustrated in FIGS. 4a and 4b.

FIG. 5 is a cross-sectional view of the leg assembly hinge, lock and upper leg section.

FIG. 6a is an end view of the leg assembly link bar.

FIG. 6b is a side view of the link bar of FIG. 6a.

FIG. 7a is an elevation view of the leg assembly in the folded condition.

FIG. 7b is a side view of the folded leg assembly of FIG. 7a, rotated 90° about the lower leg section axis.

FIG. 7c is an end view of the folded leg assembly of FIGS. 7a and 7b.

FIG. 8a is an end view of the thermal lock used in the upper leg portion of the leg assembly.

FIG. 8b is a side view of the thermal lock of FIG. 8a.

DESCRIPTION OF THE PREFERRED EMBODIMENT

Figure 1:
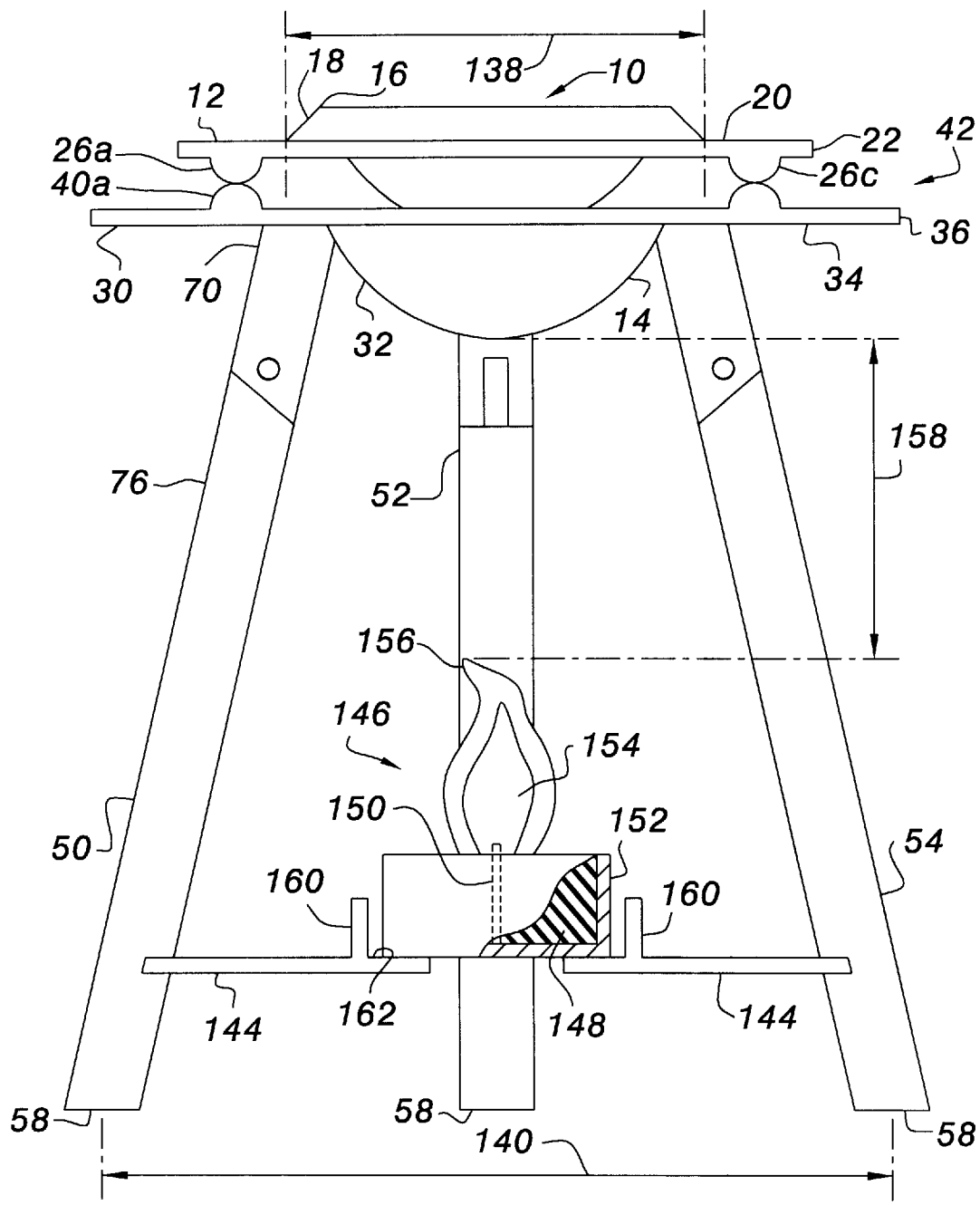
FIG. 1 is a side elevation view, in partial cross section, of the compact oil diffuser having the tripod in the open and erect position.
Figure 1A:
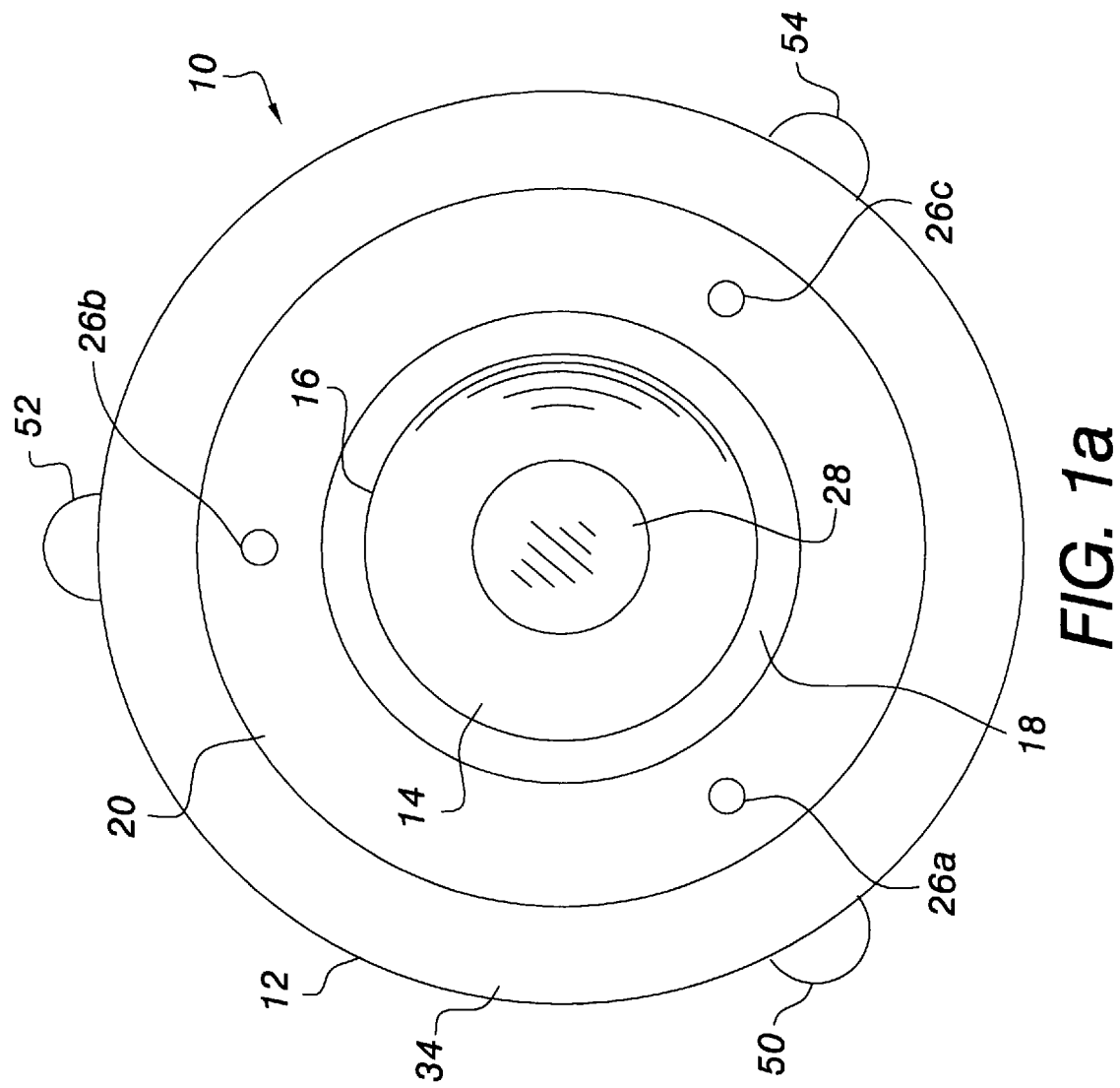
FIG. 1a is a top view of the oil diffuser of FIG. 1

Referring specifically to FIGS. 1, 1a and 3 of the accompanying drawings, a compact folding tripod oil diffuser 10 for heating and diffusing fragrance materials such as essential oils includes an oil bowl upper plate 12 having a substantially hemispherical bowl segment 14 with a circular open rim 16. Bowl segment open rim 16 preferably includes a raised sharp corner in the form of a circumferential containment ridge or wall 18 affixed to a substantially planar annular circumferential flange 20 having a circular outer edge 22 with a first selected outside diameter 24. First, second and third plate joining depressions 26a, 26b, 26c are radially arrayed upon and project transversely through the bottom surface of bowl flange 20. Bowl segment 14 is a reservoir containing and supporting the essential oil 28 (or any other fragrance material) for heating.

Oil bowl upper plate 12 is positioned coaxially above a circular lower plate heat deflector 30 and uniformly spaced apart therefrom by an air gap of uniform separation. The lower plate 30 has a substantially hemispherical indented center segment 32 affixed to a generally annular flange segment 34 having a circular outer edge 36 with a second selected outside diameter 38 being larger than the upper plate flange outside diameter 24. Since the upper plate 12 is coaxially aligned with the lower plate 30, the lower flange outer edge 36 extends radially beyond the bowl flange outer edge 22 and the upper plate oil bowl segment 14 is positioned above the lower plate indented center segment 32. Both the upper plate 12 and the lower plate 30 are preferably made of steel or an similar thermally conductive metal. First, second and third plate joining bumps 40a, 40b, 40c are radially arrayed upon and project transversely from the top surface of lower plate flange 34 and are mechanically affixed to the corresponding first, second and third plate joining depressions 26a, 26b, 26c radially arrayed upon and projecting through the bottom surface of bowl flange 20 to create a thermally conductive coupling therebetween. The bumps are coupled to the depressions by use of thermally conductive welds, solder joints, screws, rivets, or bolts. Once coupled, oil bowl upper plate 12 and heat deflecting lower plate 30 comprise a double bowl assembly 42.

First, second and third foldable leg assemblies 50, 52, 54 are illustrated in FIGS. 1, 1a, 2, 4a, 4b, 4b, 4c, 7a, 7b and 7c. Foldable leg assemblies 50, 52, 54 each have a top end 56 and a bottom end 58 and are radially arrayed in a tripod, separated by approximately 120° in angle, to define a stable platform for supporting the double bowl assembly 42. The foldable legs 50, 52, 54 are oriented at a slight angle, approximately 15° from vertical, to provide a stable base with a triangular footprint being approximately 3 to 5 inches on a side.

Turning now to FIG. 5 and FIG. 7b, it is illustrated that each of the folding legs has an upper segment 70 with an angled face 72 matching the angled face 74 on the corresponding lower leg segment 76. Upper leg segment 70 is joined to a link bar 78 by use of an upper hinge pin 80. Link bar 78 is press-fitted into a blind hole 82 in lower leg segment 76. Link bar 78 is rotatable about hinge pin 80; there is a loose fit between hinge pin 80 and a link bar transverse bore 84. Clearance for the rotating link bar end is provided by a hinge cutout segment or slot 86 in the upper leg segment 70. As shown in FIGS. 5 and 6a, link bar 78 has a detent notch 87 and flats 88 on opposing sides of the radiused link bar upper end 97 upper end thicker separated by a link bar upper end thickness selected to be slightly smaller than the width of cutout slot 86 in upper leg segment 70. When the foldable leg assembly (e.g., 50) is extended, the angled face 72 of the upper leg segment 70 joins or touches angled face 74 of lower leg segment 76.

Within upper leg segment 70 is mounted a thermal lock 100 as shown in FIGS. 8a and 8b. The thermal lock includes an accordion pleated cylindrical expandable body 112 having a flexible, resilient back plate 114 with a radially projecting lip 116 and a distally projecting pin 118 aligned with the central axis of body 112. As shown in FIG. 5, thermal lock body 112 is press fit in a blind hole 120 in upper leg segment 70 bottoming in a circumferential groove 122 of a diameter larger than the diameter of the blind hole 120. The thermal lock body 112 is located by back plate lip 116 being pressed against the face of groove 122 in upper leg segment by force from a partially compressed circular Belleville spring washer 124. Upper leg segment blind hole 120 has a diameter larger than the diameter of the thermal lock body 112 but smaller than the diameter of the thermal lock lip 116. Belleville washer 124 has a diameter smaller than the diameter of the blind hole 120 and is placed in the blind hole 120 before thermal lock 100 is inserted. Upon insertion, thermal lock lip 116 resiliently snaps into groove 122.

Figure 2:
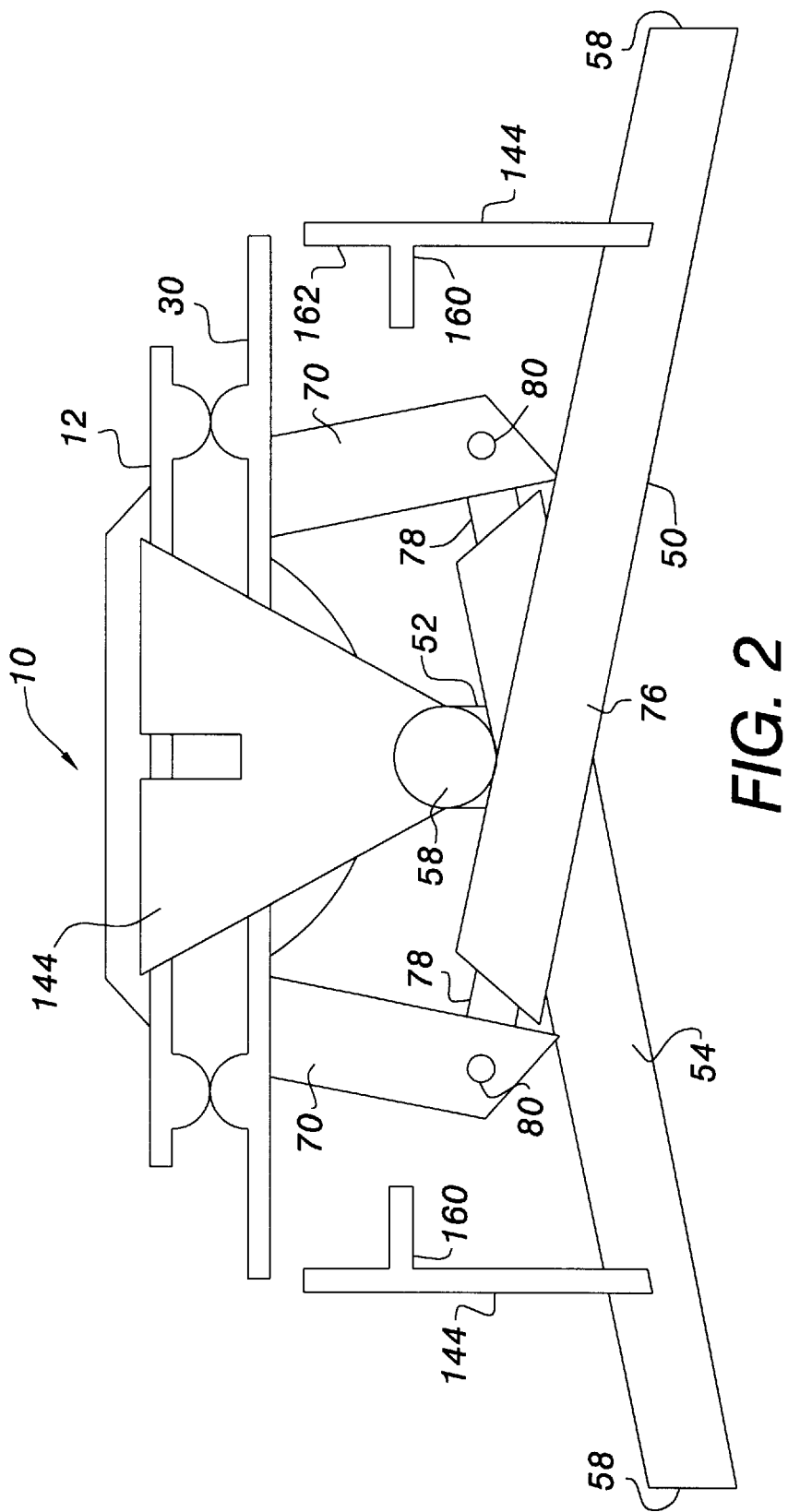
FIG. 2 is a side elevation view of the compact oil diffuser having the tripod in the closed and folded position.

The thermal lock body 112 is a hollow brass pleated cylinder filled with a paraffin material 126. The thermal lock paraffin material 126 changes phase from solid to liquid and expands substantially and increases in length at a selected temperature , The expanding length of the thermal lock body moves the thermal lock locking pin 118 distally to mate with the locking cutoff or notch 128 at the link bar upper end 90 and prevents the link bar 78 from rotating around the upper hinge pin 80. The locking pin 118 is preferably rounded to allow a detent action in both the leg extended and leg folded positions (as illustrated in FIG. 4a and FIG. 7a) even when the thermal lock body is cool (i.e., is substantially below the selected temperature). If the leg upper segment 70 and the lock body 112 are heated while the legs are folded, the thermal lock body 112 expands, thus increasing its length and compressing or deflecting the Belleville washer 124. The lower leg can be rotated from the folded position (as shown in FIGS. 2 and 7b) to the extended position (as shown in FIGS. 1 and 4b) whereupon Belleville washer 124 will push thermal lock 100 forwardly or distally and locking pin 118 will engage the locking pin cutout or notch 128 in the top of link bar 78. As noted above, link bar 78 also includes transverse, tangential detent notch 87 proximate the transverse bore 84 for accommodating the thermal lock pin 118 when the lower leg segment 76 is in the folded position (i.e., as in FIG. 7b). Belleville washer 124 allows axial movement of thermal lock body 112 for a fixed thermal lock body length and, being a spring element, allows some movement, thereby ensuring a properly centered positioning of the lower leg. A hole 134 is bored into to the top 56 of upper leg segment 70 for attachment to the lower plate 30 of the double bowl assembly 42 using screws, rivets, bolts or other aster. The leg tops 56 are radially arrayed in an equilateral triangle separated by an equal distance 138 and affixed close to the indented center segment 32 of the lower plate 30 to ensure good thermal conduction between lower plate 30 the top end 56 of each of the three foldable legs 50, 52, 54. The legs 50, 52, 54 are angled at approximately 15 degrees from vertical and aligned radially outwardly so that the leg spacing or length 140 of the sides of the equilateral triangle defined by the leg bottoms 58 is significantly larger than the spacing or distance 138 at the leg tops 56. For each of the three legs 50, 52, 54, a substantially transverse candle holder plate segment 144 is attached by welding, soldering or mechanical fastener lower leg segment 76, A candle 146 includes a wax body 148 surrounding a wick 150 and contained in a candle cup 152; as shown in FIG. 1; a flame 154 having a flame top 156 is emitted during burning of the candle 146. The candle holder plate segment 144 is located a short distance from the bottom end 58 of lower leg segment 76. The short distance (e,g., approx. one eighth inch) is sufficient to prevent candle 146 from touching the surface (e.g., table top) on which the oil diffuser 10 is to be placed. Each of the three candle holder plate segments 144 extend radially inwardly from a lower leg and has a tab 160 for centering and locating the candle 146 directly under the indented center segment 32 of the lower plate 30 when the legs 50, 52, 54 are extended. With the candle 146 supported as shown in FIG. 1, the distance 158 from the flame top 156 to the bottom of the indented center segment is, depending on flame size and wick length consumed, between approximately one and two inches. As shown in FIGS. 1 and 4b, the upward surface or face 162 is that portion of the candle holder plate segment 144 extending beyond the locating tab 160 and supporting the candle 146.

The preferred material for the upper plate 12 and the lower plate 30 is sheet steel. However, any metal of comparable thermal conductivity will suffice. It is possible to use other non-flammable material such as glass or ceramic, provided that sufficient thermal conductivity for proper operation of the oil diffuser is obtained. The leg upper and lower segments 70, 76 are preferably made from aluminum, however, steel or other metals will also suffice. The lower leg segment 76 could be made out of plastic, however, the upper leg segment must conduct heat and so a thermally conductive metal is preferable. The candle holder plate 144 should be the same material as the lower leg segment 76, to facilitate manufacture. Link bar 78 and the hinge pin 80 are preferably steel or an engineering grade of plastic having high heat tolerance and high strength. The thermal body 112 is preferably brass, however, other materials could be used.

In use, the folding essential oil diffuser 10 is expanded by opening the three folding legs 50, 52, 54 of the tripod structure and positioned on a table top, or the like. The candle 146 is placed on the candle holder plate segments 144 located in the tripod center and held in place by raised tabs 160 and supported above the surface of the table. Essential oil is poured into the reservoir or bowl 14 of the upper plate 12 and the candle 146 is lit, whereupon flame 154 from the candle heats the lower plate member 30 of the double bowl assembly 42. Heat from flame 154 is transmitted via radiation, convection and conduction from the lower plate member 30 to the upper bowl 14 and causes the oil in the oil reservoir to vaporize, thus diffusing the fragrant aromas of the essential oil into the air surrounding the diffuser. Heat is also conducted from the lower plate 30 to the upper leg segments 70 and to the thermal lock bodies 112 therein, causing the thermal lock bodies 112 in each leg to expand and forcing locking pin 118 into notch 128 in link bar 78 situated between the upper leg segments 70 and the lower leg segments 76 in each of the three legs 50, 52, 54 of the tripod. When the thermal locks are in the extended position, the link bars 78 cannot rotate about their hinge pins 80 and the legs are locked until such time as the candle flame 154 is extinguished and the lower plate 30 and thermal lock 100 have had sufficient time to cool. The operator may then remove any residual oil from the oil reservoir, whereupon the candle can be removed and the three legs can be folded for storage. In the simplest form, the method of the present invention includes the steps of: placing the fragrance material in a first thermally conductive upper member 12, placing a candle 146 providing a flame 154 in proximity to the first member 12, placing a second thermally conductive thermal diffusing lower member 30 in thermal conductive contact with the first member 12 and between the first member 12 and the candle flame 154, heating the second thermally conductive member 30 from the candle flame by radiation and convection, and heating the first member 12 from the second member 30 by conduction and convection.

A compact folding structure for an oil diffuser has been described, but a number of variations are possible. For example, any solid or liquid fragrance material can be heated. The structure can employ four or more folding legs. A triple bowl assembly can be used to further diffuse and deflect the heat of the candle flame 154.

In as much as the present invention is subject to various modifications and changes in detail, the above description of the preferred embodiment is intended to be exemplary only and not limiting.

What is claimed is:

1. A fragrance dispensing device for receiving a fragrance material and supporting the fragrance material in proximity to a heat source, comprising:

a thermally conductive reservoir bowl, wherein the fragrance material is disposed within said reservoir bowl;

a support structure supporting said reservoir bowl and defining a heat source location beneath said reservoir bowl;

a thermally conductive heat diffuser disposed between said reservoir bowl and the heat source location, wherein heat from a heat source is transmitted through said heat diffuser and into said reservoir bowl.

2. A fragrance dispensing device for receiving a fragrance material and supporting the fragrance material in proximity to a heat source, comprising:

a thermally conductive reservoir having a first width, wherein the fragrance material is disposed within said reservoir; and a support structure supporting said reservoir and defining a heat source location beneath said reservoir;

a thermally conductive heat diffuser having a second width larger than said first width, being situated apart from said reservoir by a selected distance and being disposed between said reservoir and a heat source location, wherein heat from the heat source is transmitted through said heat diffuser and into said reservoir.

3. The fragrance dispensing device of claim 2, wherein said reservoir is a bowl having an annular flange.

4. The fragrance dispensing device of claim 2, wherein said reservoir includes at least one thermally conductive projecting element.

5. The fragrance dispensing device of claim 4, wherein said heat diffuser includes at least one thermally conductive projecting element affixed by a thermally conductive coupling to said reservoir projecting element.

6. The fragrance dispensing device of claim 2, wherein said reservoir includes a peripheral containment wall.

7. The fragrance dispensing device of claim 2, wherein said support structure includes first, second and third support legs, wherein said support structure supports said reservoir, said heat diffuser, and said heat source.

8. The fragrance dispensing device of claim 7, wherein at least one of said support legs includes a hinge and is foldable at said hinge.

9. The fragrance dispensing device of claim 8, wherein said foldable support leg further includes a thermal lock; wherein said lock enables the hinge when said leg is at a first selected temperature and disables said hinge when said leg is at a second selected temperature being higher than said first selected temperature.

10. A fragrance dispensing device for receiving a fragrance material and supporting the fragrance material in proximity to a heat source, comprising:

a thermally conductive reservoir having a first width, an annular flange and at least one thermally conductive projecting element, wherein the fragrance material is disposed within said reservoir;

a support structure having first, second and third folding support legs supporting said reservoir and defining a heat source location beneath said reservoir;

a thermally conductive heat diffuser having a second width larger than said first width, being situated from said reservoir by a selected distance and being disposed between said reservoir and the heat source location, wherein said heat diffuser includes at least one thermally conductive projecting element affixed by a thermally conductive coupling to said reservoir projecting element, wherein heat from a heat source is transmitted through said heat diffuser and into said reservoir.

11. The fragrance dispensing device of claim 10, wherein said thermally conductive coupling is a screw, bolt, rivet or weld.

12. The fragrance dispensing device of claim 10, wherein said foldable legs include a hinge and a thermal lock; wherein said thermal lock disables said hinge when said leg temperature is above a selected temperature.

13. The fragrance dispensing device of claim 12 wherein said thermal lock comprises a thermally conductive resilient body filled with a paraffin phase change material.

14. The fragrance dispensing device of claim 10, wherein said support legs include a radially projecting inwardly extending candle holder plate section.

15. The fragrance dispensing device of claim 14, wherein each said support leg radially projecting inwardly extending candle holder plate section includes a transverse containment tab.

16. The fragrance dispensing device of claim 10, wherein the fragrance material is a liquid.

17. The fragrance dispensing device of claim 16, wherein said liquid is an essential oil.

18. A heating device including first, second and third support legs, wherein said first support leg includes a hinge and is foldable at said hinge; and wherein said foldable first support leg further includes a thermal lock; wherein said lock enables the hinge when said leg is at a first selected temperature and disables said hinge when said leg is at a second selected temperature higher than said first selected temperature.

19. The heating device of claim 18, wherein said thermal lock includes a hollow body filled with a paraffin material, said paraffin material expanding in volume in response to an increase in hollow body temperature to a temperature equal to or greater than said second selected temperature.

20. A method for diffusing a fragrance material in the proximity of a candle flame, the method comprising the steps of:

placing the fragrance material in a first thermally conductive member;

placing a candle providing a flame in proximity to said first member;

placing a second thermally conductive thermal diffusing member in thermal conductive contact with said first member and between said first member and said candle flame;

heating said second thermally conductive member from said candle flame by radiation and convection; and heating said first member from said second member by conduction and convection.

* * * * *